US010600137B2

(12) United States Patent
Ghosh et al.

(10) Patent No.: US 10,600,137 B2
(45) Date of Patent: Mar. 24, 2020

(54) SYSTEMS AND METHODS FOR DYNAMIC AMBULANCE DEPLOYMENT

(71) Applicant: MasterCard International Incorporated, Purchase, NY (US)

(72) Inventors: Debashis Ghosh, Charlotte, NC (US); Manash Bhattacharjee, Jersey City, NJ (US)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 1019 days.

(21) Appl. No.: 15/059,002

(22) Filed: Mar. 2, 2016

(65) Prior Publication Data
US 2017/0256013 A1    Sep. 7, 2017

(51) Int. Cl.
| G06Q 50/22 | (2018.01) |
| G06Q 20/34 | (2012.01) |
| G08G 1/00 | (2006.01) |
| G06Q 20/32 | (2012.01) |

(52) U.S. Cl.
CPC ......... *G06Q 50/22* (2013.01); *G06Q 20/3224* (2013.01); *G06Q 20/34* (2013.01); *G08G 1/202* (2013.01)

(58) Field of Classification Search
CPC .............. G06F 3/0482; G06F 3/04817; G06F 3/04845; G06F 2203/04806
USPC .......................................................... 705/3
See application file for complete search history.

(56) References Cited

U.S. PATENT DOCUMENTS

| 5,812,959 | A | 9/1998 | Froeburg et al. |
| 6,058,370 | A | 5/2000 | Church et al. |
| 6,233,517 | B1 | 5/2001 | Froeberg |
| 8,442,807 | B2 | 5/2013 | Ramachandran |
| 8,786,605 | B1 | 7/2014 | Curtis et al. |
| 9,071,940 | B2 | 6/2015 | Ramachandran |
| 2012/0053887 | A1* | 3/2012 | Nurmi ................... G06F 3/0485 702/150 |
| 2012/0259540 | A1* | 10/2012 | Kishore ................. G06Q 10/06 701/410 |
| 2014/0203909 | A1 | 7/2014 | Elgebaly et al. |

(Continued)

FOREIGN PATENT DOCUMENTS

WO    2015157487 A1    10/2015

*Primary Examiner* — Reginald R Reyes
(74) *Attorney, Agent, or Firm* — Armstrong Teasdale LLP (57) ABSTRACT

A dispatcher command center for dynamic ambulance deployment based on population density is described herein. The dispatcher command center is configured to display a street map of a coverage area, the street map including a first representation of a likely population density within the coverage area, and display an ambulance location of a plurality of ambulances. The dispatcher command center is also configured to receive, in real-time, a data signal including transaction data associated with a transaction. The transaction data includes a transaction location and transaction time and represents an activity executed by a person within the coverage area. The dispatcher command center is further configured to display a second representation of the transaction at a location on the street map corresponding to the transaction location, and deploy at least one of the plurality of ambulances in response to the displayed second representation, thereby updating at least one ambulance location.

17 Claims, 6 Drawing Sheets

(56) References Cited

U.S. PATENT DOCUMENTS

2015/0120176 A1    4/2015  Curtis et al.
2017/0228499 A1*  8/2017  Baudino ................ G16H 10/60

* cited by examiner

SYSTEMS AND METHODS FOR DYNAMIC AMBULANCE DEPLOYMENT

BACKGROUND

This invention relates generally to ambulance deployment and, more particularly, to a network-based system and method for dynamic deployment of ambulances and emergency services using consumer-related data.

For Emergency Medical Services (EMS), including public or private ambulances staffed with Emergency Medical Technicians (EMTs), timing is everything. A few minutes can mean the difference between life and death. Accordingly, private EMS are subject to stringent contracts that stipulate a maximum amount of time for ambulance arrival in response to an emergency call (a "maximum response time"). Failure to meet the contracted response time often results in a per-minute fine. For example, if the maximum response time is 10 minutes, and the ambulance arrives in 13 minutes, the ambulance operator may be subjected to a $10/minute fine for any penalty minutes. (In some cases, there are allowable exclusions, such as the ambulance being stopped by a train or an accident holding up traffic, so in the above example, there may be three "late minutes" but one or two minutes of allowable exclusions, such that the ambulance operator may not be charged the penalty fine for all three late minutes.)

Due to the high cost of ambulance operation, which can reach a half a million dollars per staffed ambulance per year, EMS companies want to serve their respective communities with as few ambulances as are required while still meeting patient-care standards (e.g., the contract response time described above). A common strategy is to deploy ambulances in specific positions about a coverage area, from which they can reach the greatest number of people within the contract response time. Accordingly, ambulances are commonly placed in areas with the highest population density, relative to other areas of the coverage area. Ambulance dispatchers and/or operators (used interchangeably herein) are responsible for determining the optimal ambulance placements to meet this strategy. Typically, they rely on historical dispatch data including past emergency calls, semi-empirical data (e.g., a city or urban area is more populated during employment hours, and suburbs are more populated during non-employment hours) as well as available data identifying potential high-density events that may cause an anomalous congregation of people (e.g., newspapers or local websites that describe upcoming fairs, concerts, etc.). Reviewing this available data to identify these events, however, requires time and effort to analyze and schedule around. In addition, ambulance dispatchers may be unaware of certain high-density events, as the event may be relatively short notice and/or may not be well publicized. It would be beneficial for ambulance dispatchers and to for communities they service to have a system configured to supplement existing ambulance deployment schemes to reduce ambulance response times.

BRIEF DESCRIPTION

In one aspect, a dispatcher command center for dynamic ambulance deployment based on population density is provided. The dispatcher command center includes a display device and a processor in communication with a memory. The processor is programmed to display, on the display device, a street map of a coverage area. The street map includes a first representation of a likely population density within the coverage area at a point in time. The processor is also programmed to display, on the display device, an ambulance location of a plurality of ambulances relative to the street map. The processor is further programmed to receive, in real-time, a data signal including transaction data associated with a transaction. The transaction data includes a transaction location and transaction time and represents an activity executed by a person within the coverage area. The processor is also programmed to display, on the display device, a second representation of the transaction at a location on the street map corresponding to the transaction location. The processor is still further programmed to deploy at least one of the plurality of ambulances in response to the displayed second representation, thereby updating at least one corresponding ambulance location relative to the street map.

In another aspect, a computer-implemented method for dynamically deploying ambulances based on population density is provided. The method is implemented using a dispatcher command center including a display device and a processor in communication with a memory. The method includes displaying, on the display device, a street map of a coverage area. The street map includes a first representation of a likely population density within the coverage area at a point in time. The method also includes displaying, on the display device, an ambulance location of a plurality of ambulances relative to the street map, and receiving, in real-time, a data signal including transaction data associated with a transaction. The transaction data includes a transaction location and transaction time and represents an activity executed by a person within the coverage area. The method further includes displaying, on the display device, a second representation of the transaction at a location on the street map corresponding to the transaction location, and deploying at least one of the plurality of ambulances in response to the displayed second representation, thereby updating at least one corresponding ambulance location relative to the street map.

In yet another aspect, at least one non-transitory computer-readable storage media having computer-executable instructions embodied thereon is provided. When executed by at least one processor in communication with a memory, the computer-executable instructions cause the processor to display, on a display device, a street map of a coverage area. The street map includes a first representation of a likely population density within the coverage area at a point in time. The computer-executable instructions also cause the processor to display, on the display device, an ambulance location of a plurality of ambulances relative to the street map. The computer-executable instructions further cause the processor to receive, in real-time, a data signal including transaction data associated with a transaction. The transaction data includes a transaction location and transaction time and represents an activity executed by a person within the coverage area. The computer-executable instructions also cause the processor to display, on the display device, a second representation of the transaction at a location on the street map corresponding to the transaction location, and deploy at least one of the plurality of ambulances in response to the displayed second representation, thereby updating at least one corresponding ambulance location relative to the street map.

BRIEF DESCRIPTION OF THE DRAWINGS

FIGS. 1-6 show example embodiments of the methods and systems described herein.

Like numbers in the Figures indicate the same or functionally similar components.

DETAILED DESCRIPTION

The ambulance deployment system described herein is configured to receive a real-time transaction data signal (e.g., transaction volume) and configure that signal for display to an ambulance dispatcher for identification of locations within an ambulance coverage area (e.g., a city or portion thereof) that have a relatively high population density. The ambulance deployment system thereby facilitates flexible, prompt, pre-emptive, and dynamic ambulance deployment to those high-density locations. The transaction data is representative of a population density because a consumer is present at a merchant location (or other transaction location) when the transaction is performed. In addition, the ambulance deployment system may be configured to transmit an alert to the ambulance dispatcher when a particular location or "zone" within the coverage area experiences particularly high population density.

In the example embodiment, the ambulance deployment system includes a dispatcher "command center," which is configured to display ambulance locations to an ambulance dispatcher. The dispatcher command center includes a computer system, itself including a processor and a memory device, and a display device (e.g., a monitor). The dispatcher command center displays ambulance locations on a map of the designated coverage area (e.g., a street map and/or geographical map of the coverage area), referred to herein as a "street map." The dispatcher command center also displays the relative population density across the coverage area. The relative population density may be displayed, for example, as a "heat map" overlaid on the street map of the coverage area (or, for example, as a contour or surface plot). The relative population density is determined as a function of historical dispatch data parsed from emergency calls, which is representative of a likely population density of people at a particular point in time. The display population density may further account for semi-empirical data related to the movement of people over the course of a day (e.g., higher population density in urban areas during employment hours, higher population density in suburban areas during non-employment hours, known high-density events such as sporting events or concerts) and other probabilistic analyses that attempt to predict the most likely locations of ambulance deployment.

In the example embodiment, the dispatcher command center is further in communication with a payment processor (e.g., an interchange network or other network for processing payment transactions). The payment processor is configured to process payment transactions. Each transaction is initiated by a cardholder using a payment card associated with an issuing bank, and may have additional data associated therewith ("transaction data"). Transaction data includes such elements as a transaction amount, a merchant identifier, an account identifier (associating the transaction with a cardholder), a time and date stamp, and a location identifier, which may identify where the transaction was initiated (i.e., a location of the cardholder) and/or the location of the merchant. The dispatcher command center receives, in real-time, a data signal including transaction data associated with a plurality of transactions initiated within the coverage area. The dispatcher command center processes the received transaction data and generates a transaction record associated with each transaction initiated within the coverage area. Each transaction record includes a transaction time and transaction location of the corresponding financial transaction. "Real-time" refers to outcomes occurring at a substantially short period after an input. The time period is a result of the capability of the ambulance deployment system (i.e., the transaction processor and the dispatcher command center) implementing processing of the inputs to generate the outcome. Events occurring in real-time occur without substantial intentional delay.

The dispatcher command center is configured to display representations of the generated transaction records on the display device to the dispatcher relative to the street map. In certain embodiments, the dispatcher command center is configured to modify the original street map to include transaction records. For example, if the original street map is a heat map, wherein "hotter" zones (e.g., darker colors, "more red" colors, etc.) indicate higher population density, the dispatcher command center may generate instructions to "heat" the street map at a location corresponding to the transaction location of each transaction record. More "heat" is added for each individual transaction record, such that high-density zones rapidly become "hot zones," which are readily visible to the ambulance dispatcher on the street map. In other embodiments, the dispatcher command center may generate a separate, "secondary" street map to display on the display device alongside the "primary" street map described above, wherein the secondary street map includes only the real-time representations of transaction records. Because the transaction data signal can be provided to show transaction records in real time or near real time at the dispatcher command center, population density can also be shown in real time or near real time. Moreover, the ambulance deployment system described herein is configured to show trends of population density. In other word, the system is configured to show how the population may shift between zones within the coverage area over a period of time.

Each transaction record may be configured to "expire" after a predetermined period of time (e.g., ten minutes, one hour, two hours, one day) after a time stamp associated therewith. As the dispatcher command center may continually receive the transaction data signal from the payment processor for display of transaction records substantially in real-time, the dispatcher command center is configured to continually update the street map. More specifically, the dispatcher command center is configured to add heat or other indicators to the street map corresponding to each generated transaction record, and remove heat or other indicators from the street map for each expired transaction record.

In certain embodiments, the dispatcher command center is configured to generate alerts for particularly high-density zones. The dispatcher command center may, for example, divide the coverage area into a plurality of zones. Each zone may encompass a defined geographic area (e.g., a city block) and/or may encompass one or more merchants (e.g., potential transaction locations). The dispatcher command center maps the transaction location(s) of the plurality of transaction records to corresponding zones. In one embodiment, each transaction record mapped to a zone increments a counter associated with that zone. The dispatcher command center is further configured to define a high-density condition. If a zone meets the high-density condition, the zone is identified as a "high-density zone." The high-density condition may include a threshold value reached by the counter for the zone. Upon the identification of a high-density zone, the dispatcher command center generates an alert identifying the high-density zone. The alert may be displayed on the street map, for example, as an icon or other visual indicator of the zone. Additionally or alternatively, the high-density indicator may include a textual description or identification of the high-density zone (e.g., "High traffic at $5^{th}$ and Elm").

By supplementing or augmenting existing historic dispatch data and probabilistic maps with real-time transaction traffic, an ambulance dispatcher may readily identify unexpected or unscheduled high population-density zones or events. The street map that is output at the display device of the dispatcher command center facilitates rapid identification of clusters of transaction records or "high-heat" zones that would not have been displayed or identified otherwise. The ambulance dispatcher may then dynamically adjust the location(s) of deployed ambulances in order to best cover the high-density zones, such that response time may decrease and emergencies may be more readily resolved. For example, in response to the representations of transaction records at a particular location, the dispatcher may deploy one or more ambulance(s) to or near that location. The location of the corresponding ambulance(s) relative to the street map at the dispatcher command center will be accordingly updated. In certain embodiments, the ambulance dispatcher may utilize the street map to dynamically deploy "flexible" ambulances, which are variably dispatched to locations corresponding to the greatest need, in order to supplement the coverage ranges of "fixed" ambulances (i.e., those ambulances that remain at stations, similar to fire stations, until they are deployed for a call).

At least one of the technical problems addressed by this system includes: (i) reliance on out-dated, untimely, or inaccurate population density information used in deploying ambulances or other emergency vehicles; (ii) lagging response times due to inefficiently deployed ambulances; and (iii) lack of preparedness for unknown high-density events or locations within an ambulance coverage area.

A technical effect of the systems and processes described herein is achieved by performing at least one of the following steps: (i) displaying a street map of a coverage area, the street map including a first representation of a likely population density within the coverage area at a point in time; (ii) displaying an ambulance location of a plurality of ambulances relative to the street map; (iii) receiving, in real-time, a data signal including transaction data associated with a transaction, the transaction data including a transaction location and transaction time, the transaction data representing an activity executed by a person within the coverage area; (iv) displaying, on the display device, a second representation of the transaction at a location on the street map corresponding to the transaction location; and (v) deploying at least one of the plurality of ambulances in response to the displayed second representation, thereby updating at least one corresponding ambulance location relative to the street map.

The technical effect achieved by this system is at least one of: (i) improved ambulance deployment targeting unexpected or otherwise unrecognized high-density zones to better meet the emergency needs of a community; (ii) more reliable and/or timely estimation of a density of people at a location; (iii) enhanced identification of zones in need of ambulance deployment in advance of increased emergency calls; and (iv) reduction in response times of flexibly deployed ambulances.

As used herein, the term "authentication" (or an "authentication process") is used generally to refer to a process conducted on a payment transaction prior to the "authorization" of a transaction (or an "authorization process"). At least one purpose of the authentication process is to evaluate whether or not the person conducting the transaction is actually a person privileged to use the payment card presented in the transaction. An authentication process may be used to reduce fraudulent transactions, and thus protect one or more parties to the transaction (e.g., the merchant, or the issuer of the payment card).

As used herein, a processor may include any programmable system including systems using micro-controllers, reduced instruction set circuits (RISC), application specific integrated circuits (ASICs), logic circuits, and any other circuit or processor capable of executing the functions described herein. The above examples are example only, and are thus not intended to limit in any way the definition and/or meaning of the term "processor."

As used herein, the terms "software" and "firmware" are interchangeable, and include any computer program stored in memory for execution by a processor, including RAM memory, ROM memory, EPROM memory, EEPROM memory, and non-volatile RAM (NVRAM) memory. The above memory types are example only, and are thus not limiting as to the types of memory usable for storage of a computer program.

In one embodiment, a computer program is provided, and the program is embodied on a computer readable medium. In an example embodiment, the system is executed on a single computer system, without requiring a connection to a sever computer. In a further embodiment, the system is being run in a Windows® environment (Windows is a registered trademark of Microsoft Corporation, Redmond, Wash.). In yet another embodiment, the system is run on a mainframe environment and a UNIX® server environment (UNIX is a registered trademark of X/Open Company Limited located in Reading, Berkshire, United Kingdom). The application is flexible and designed to run in various different environments without compromising any major functionality. In some embodiments, the system includes multiple components distributed among a plurality of computing devices. One or more components may be in the form of computer-executable instructions embodied in a computer-readable medium. The systems and processes are not limited to the specific embodiments described herein. In addition, components of each system and each process can be practiced independent and separate from other components and processes described herein. Each component and process can also be used in combination with other assembly packages and processes.

As used herein, the terms "transaction card," "financial transaction card," "payment card," and "payment device" refer to any suitable transaction card, such as a credit card, a debit card, a prepaid card, a charge card, a membership card, a promotional card, a frequent flyer card, an identification card, a prepaid card, a gift card, and/or any other device that may hold payment account information, such as mobile phones, Smartphones, personal digital assistants (PDAs), wearable computing devices, key fobs, digital wallets, and/or computers. Each type of transactions card can be used as a method of payment for performing a transaction. As used herein, the term "payment account" is used generally to refer to the underlying account with the payment device. In addition, account-holder behavior can include but is not limited to purchases, management activities (e.g., balance checking), bill payments, achievement of targets (meeting account balance goals, paying bills on time), and/or product registrations (e.g., mobile application downloads).

The following detailed description illustrates embodiments of the disclosure by way of example and not by way of limitation. It is contemplated that the disclosure has general application to processing financial transaction data by a third party in industrial, commercial, and residential applications.

As used herein, an element or step recited in the singular and preceded with the word "a" or "an" should be understood as not excluding plural elements or steps, unless such exclusion is explicitly recited. Furthermore, references to "example embodiment" or "one embodiment" of the present disclosure are not intended to be interpreted as excluding the existence of additional embodiments that also incorporate the recited features.

Figure 1:
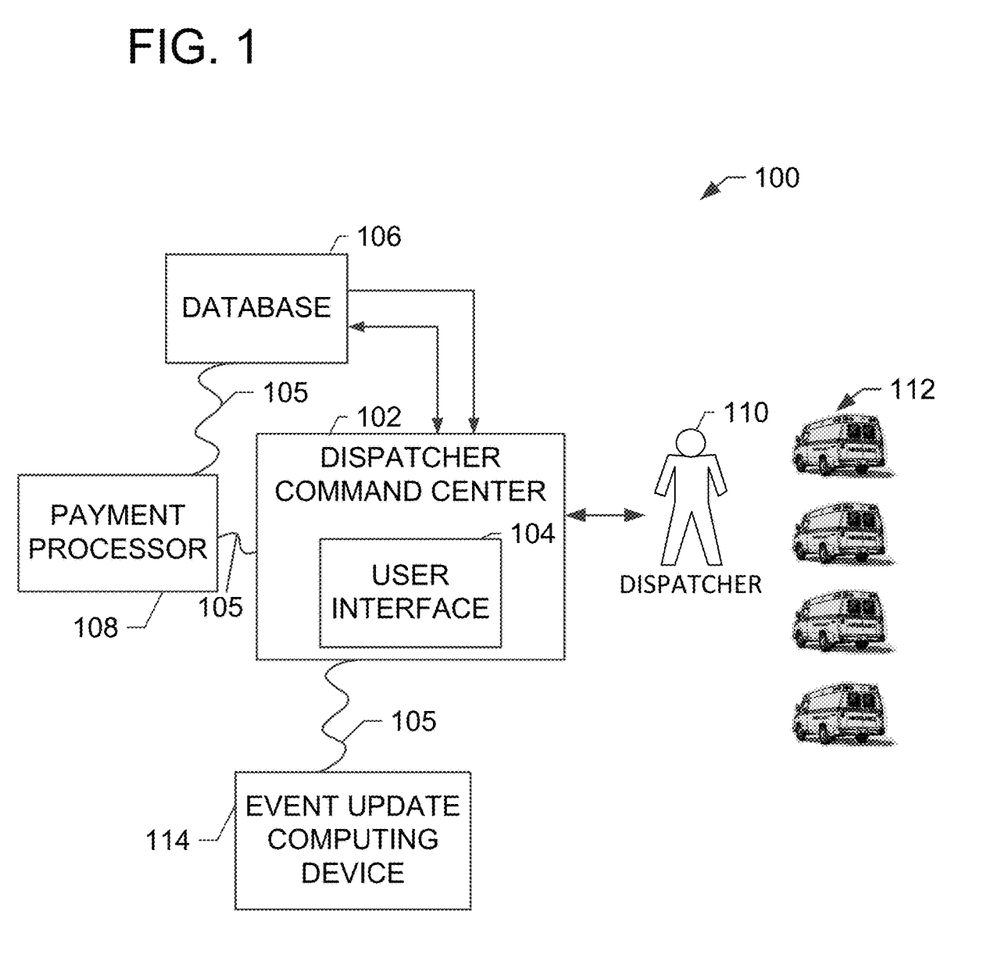
FIG. 1 is a simplified schematic block diagram of an ambulance deployment system for facilitating dynamic ambulance deployment using transaction data received from a payment processor.

FIG. 1 is a simplified block diagram of an example ambulance deployment system 100 for facilitating dynamic ambulance deployment to high-traffic locations using a dispatcher command center 102. In the example embodiment, dispatcher command center 102 includes a computing device located within an emergency medical services (EMS) entity responsible for deploying a plurality of ambulances 112 to locations within a coverage area. In other embodiments, dispatcher command center 102 represents multiple computing devices that may be located elsewhere but that provide information as described herein to a user (dispatcher) 110 of dispatcher command center 102.

In the example embodiment, dispatcher command center 102 is in communication with a database 106 and a payment processor 108. Payment processor 108 is associated with and/or integral to payment processing network (not shown). In a typical transaction card system, a financial institution called the "issuer" issues a transaction card, such as a credit card, to a consumer or cardholder, who uses the transaction card to tender payment for a purchase from a merchant. To accept payment with the transaction card, the merchant must normally establish an account with a financial institution that is part of the financial payment system. This financial institution is usually called the "merchant bank," the "acquiring bank," or the "acquirer." When the cardholder tenders payment for a purchase with a transaction card, the merchant requests authorization from a merchant bank for the amount of the purchase, for example, by receiving account information associated with the cardholder and communicating the account information to the merchant bank. Using payment processor 108, the merchant will communicate with the issuer bank to determine whether the cardholder's account is in good standing and whether the purchase is covered by the cardholder's available credit line. Based on these determinations, the request for authorization will be declined or accepted. If a request for authorization is accepted, the available credit line of the cardholder's account is decreased. If the cardholder uses a debit card, the available funds in the cardholder's account will be decreased. Payment processor 108 may store the transaction card information, such as a type of merchant, amount of purchase, date of purchase, in database 106.

After a purchase has been made, a clearing process occurs to transfer additional transaction data related to the purchase among the parties to the transaction. More specifically, during and/or after the clearing process, additional data, such as a time of purchase, a merchant name, a type of merchant, purchase information, account-holder account information, a type of transaction, savings information, information regarding the purchased item and/or service, and/or other suitable information, is associated with a transaction and transmitted between parties to the transaction as transaction data. Payment processor 108 may store the transaction data in database 106 and/or may transmit the transaction data to dispatcher command center 102. Dispatcher command center 102 and payment processor 108 are interconnected to the Internet through many interfaces including a network 105, such as a local area network (LAN) or a wide area network (WAN), dial-in-connections, cable modems, special high-speed Integrated Services Digital Network (ISDN) lines, and RDT networks.

Payment processor 108 is configured to process transaction data generated in association with a plurality of financial transactions as described above. Transaction data includes such elements as a transaction amount; a merchant identifier; an account identifier (associating the transaction with the cardholder); a time and date stamp; and a location identifier, which may identify where the transaction was initiated, a location of the cardholder at the time the transaction was initiated, and/or the location of the merchant (e.g., the POS device). The transaction data includes information associated with a processed transaction and is representative of consumer activity at a particular geographic location. Accordingly, payment processor 108 transmits the transaction data to dispatcher command center 102 to provide accurate, real-time representations of consumer activity, and thereby population density, at merchant locations within a coverage area. Where "transaction location" is used herein, it may refer to a merchant location and/or a cardholder location associated with the transaction. For example, for "card-present" transactions, the merchant location is indicative of where the consumer or cardholder was during the transaction, and accordingly is indicative of a population at the merchant location. For "card-not-present" transactions, such as online purchases, the cardholder location (e.g., IP address, GPS location, etc.) is indicative of where the consumer or cardholder is, even if the merchant location associated with the transaction may not be within the coverage area.

As used herein, "coverage area" refers generally to a geographic area covered by an EMS station or set of stations. For example, one EMS may have several buildings or stations with ambulances 112 housed therein (prior to deployment to an emergency) as well as a plurality of ambulances 112 that are not located at stations but are deployed throughout the coverage area. The coverage area may represent an entire city or a portion thereof, or portions of adjoining cities within a county, etc. Coverage areas may vary depending on population densities. For example, in a densely populated city, a coverage area may represent a dozen square miles, whereas in a suburban area, a coverage area may span a much larger area. In the example embodiment, dispatcher command center 102 is configured to divide the coverage area into a plurality of "zones." In one embodiment, dispatcher command center 102 divides the coverage area into a plurality of zones with equal area, for example, as a grid. In another embodiment, dispatcher command center 102 divides the coverage area into zones more contextually, for example, according to population density, number of buildings located therein, a number of blocks encompassed thereby, etc.

Dispatcher command center 102 is connected to database 106, which contains information on a variety of matters, as described below in greater detail. In one embodiment, centralized database 106 is stored on dispatcher command center 102. In an alternative embodiment, database 106 is stored remotely from dispatcher command center 102 and may be non-centralized. Database 106 may include a single database having separated sections or partitions or may include multiple databases, each being separate from each other. In one embodiment, database 106 may store street maps, records of emergency calls, event identifier and schedules, semi-empirical analyses including schedules of population shifts according to temporal or other external occurrences and/or additional information as described herein. In the example embodiment, database 106 may further store transaction data received from payment processor 108 ("raw transaction data") and/or a plurality of transaction records generated by dispatcher command center 102, each transaction record associated with one of the plurality of transactions and including a transaction location and time stamp. Database 106 may be configured to store transaction records for a particular period of time from the time stamp, or for an "expiration time," at which time database 106 may delete an expired transaction record therefrom. In other embodiments, database 106 may store each transaction record indefinitely. In the example embodiment, each transaction record contains no personally identifiable information (PII) of cardholders initiating the transactions and/or accounts thereof.

Dispatcher command center 102 is configured to receive transaction data form payment processor 108 and/or retrieve transaction data stored in database 106. In the example embodiment, dispatcher command center 102 receives transaction data associated with transactions initiated at merchant locations within the coverage area associated with dispatcher command center 102. "Merchant location" may refer to permanent or semi-permanent (e.g., seasonal) brick-and-mortar locations as well as "temporary" merchant locations, such as "pop-up" shops, merchants operating at booths at events, or garages sales and the like. In one embodiment, dispatcher command center 102 is configured to receive "pre-filtered" transaction data from payment processor 108, or transaction data that payment processor 108 has already identified as being associated with the coverage area. In another embodiment, dispatcher command center 102 is configured to receive transaction data not specifically associated with the coverage area, and to parse the transaction data (e.g., using a merchant identifier, merchant location, and/or transaction location of each transaction) to identify a portion of the received transaction data that is associated with the coverage area. In such an embodiment, dispatcher command center 102 may discard any received transaction data not associated with the coverage area.

Dispatcher command center 102 is further configured to process the received transaction data to identify a transaction location corresponding to each transaction. Dispatcher command center 102 generated and stores a transaction record of each transaction including the corresponding transaction location and a transaction time. In some embodiments, dispatcher command center 102 is configured to calculate an expiration time for each transaction record. The expiration time may be calculated by adding a predetermined constant time interval to the transaction time (e.g., 15 minutes, 30 minutes, 4 hours, etc.) or may be calculated by adding a non-constant time interval to the transaction time. For example, the added time interval may be shortened or lengthened according to a number of transaction records generated within a period of time (e.g., according to a frequency of transactions) and/or a number of transaction records generated that are associated with a particular zone within the coverage area (e.g., according to a density of transactions).

Dispatcher command center 102 includes a user interface (UI) 104 to facilitate communication between dispatcher command center 102 and user (dispatcher) 110. For example, UI 104 includes a display device (or other media output) to display at least one map of the coverage area to dispatcher 110 for dynamic deployment of ambulances 112. UI 104 may further include an input device to receive commands and/or requests from dispatcher 110. In the example embodiment, dispatcher command center 102 displays a street map of the coverage area on the UI 104 to dispatcher 110. In some embodiments, dispatcher 110 may be able to manipulate the displayed street map (e.g., zoom in, zoom out, pan, etc.). The street map includes information such as historical and/or current dispatch or emergency call information, which may be representative of a likely population density within the coverage area at a particular point in time. The street map may further account for semi-empirical data related to the expected location of people over the course of a day (e.g., higher traffic in urban areas during employment hours, higher traffic in suburban areas during non-employment hours, known high-density events such as sporting events or concerts) and other probabilistic analyses that attempt to predict the most likely location to need ambulance deployment thereto. The street map may further include an icon or other indicator of a location of each ambulance 112 in the coverage area, such that dispatcher 110 may accurately judge whether ambulances 112 are deployed at optimal locations to suit the needs of the people within the coverage area.

In the illustrated embodiment, dispatcher command center 102 is further in communication with an event update computing device 114, which transmits event records and/or other information (as described herein) to dispatcher command center 104. Event records include information about upcoming events the event update computing device 114 has parsed from available sources (e.g., newspapers, social media, newsletters, etc.). Event records may include locations and times associated with events likely to draw relatively high numbers of people thereto, including, but not limited to, sporting events, concerts, conventions, plays, and other such events. In certain embodiments, event update computing device 114 is configured to receive input from a plurality of available sources and parse the input for information about upcoming events. Additionally or alternatively, event update computing device 114 may include web-crawling functionality, such that event update computing device 114 may search, parse, and/or index websites for information about upcoming events associated with the coverage area.

Dispatcher command center 102 is configured to augment, enhance, or update the displayed representation of population density on the street map with representations of the transaction records. Dispatcher command center 102 may additionally or alternatively be configured to display a separate, secondary map with representations of the transaction records. Accordingly, wherein dispatcher command center 102 is described as displaying any information on the street map, such a reference may include one or both of these display methods. In so doing, dispatcher command center 102 supplements and enhances the above-described historical dispatch and/or semi-empirical data with representations of real-time population density based on transaction traffic. It should be understood that although the example embodiment is described with respect to financial transactions, dispatcher command center 102 may be further configured to receive and process additional and/or or alternate kind of consumer-related data that are representations of activities executed by persons within the coverage area, which may be generally and collectively referred to as "transactions" (e.g., vehicle locations, actions on social media, Internet use or web traffic, etc.). Such transactions may be representative of real-time population density. Each data point, or transaction record, may be discretely displayed on the street map and/or otherwise displayed. For example, each transaction record may be displayed as an icon at a location on the street map corresponding to the transaction location of the transaction record. As an alternative example, the street map may include a "heat map," wherein "hotter" areas of the heat map represent higher population density. In such an example, the transaction records may be displayed by increasing the "heat" of the heat map in a location on the map corresponding to the transaction location of the transaction record. Accordingly, dispatcher 110 may view the street map with the indications of the transaction records thereon and may more precisely deploy ambulances 112 to zones of greatest population density (as represented by the transaction records).

It should be understood that although the methods and systems disclosed herein are described with respect to the deployment of ambulances, the disclosure is readily applicable to other emergency (or non-emergency) services that may benefit from real-time population density information. For example, but without limitation, the methods and systems may be applicable to other EMS services, police or law-enforcement services, and/or emergency alert services. In such cases, these other services may utilized stored, received, retrieved, and/or otherwise accessed historical information associated with their services, which may then be supplemented using the real-time transaction data as processed and displayed by the dispatcher command center.

Figure 2:
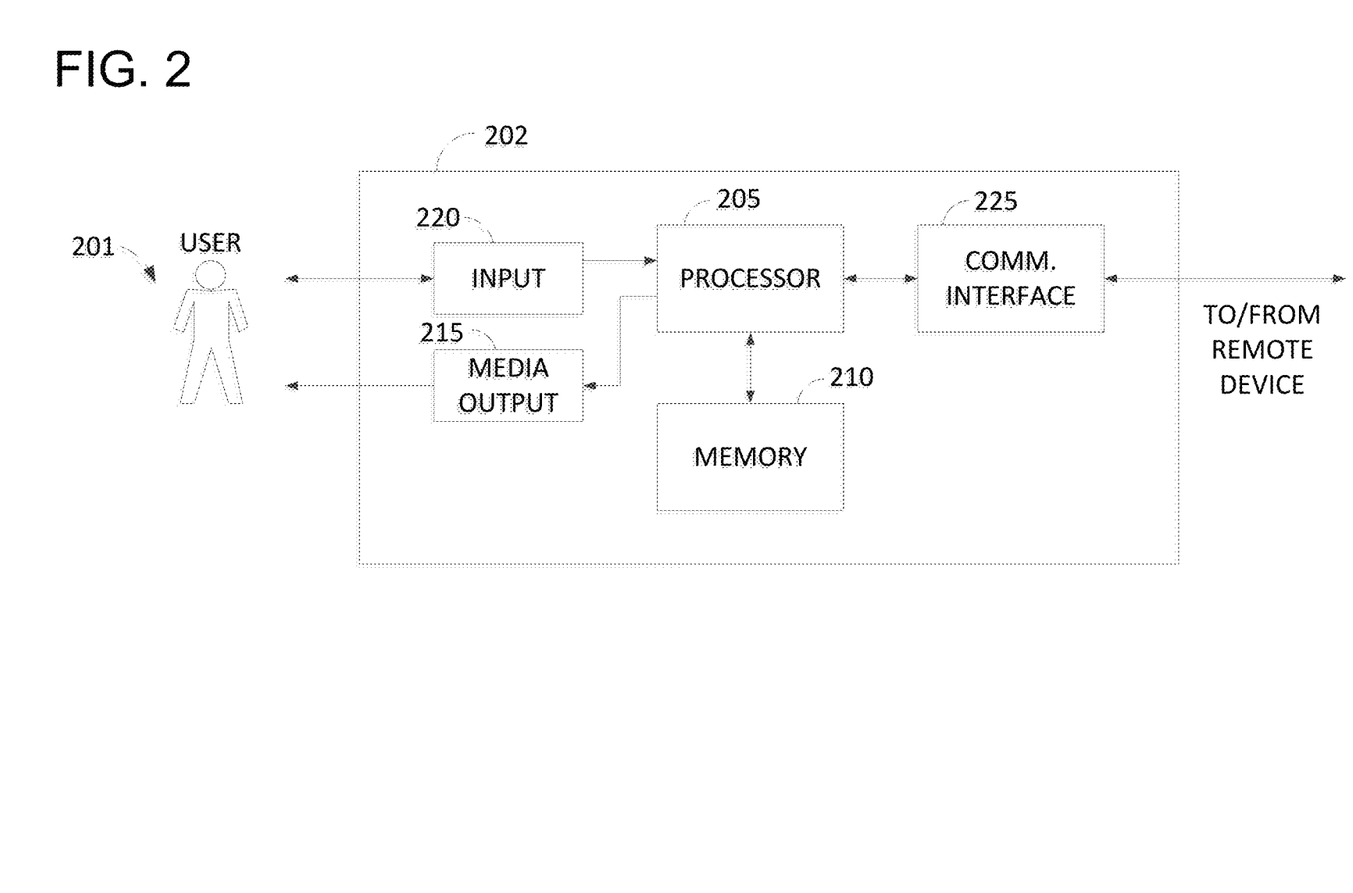
FIG. 2 illustrates an example configuration of a user system that may be used in the ambulance deployment system shown in FIG. 1.

FIG. 2 illustrates an example configuration of a user system 202 operated by a user 201, such as dispatcher 110 (shown in FIG. 1) and/or any other user. In some embodiments, user system 202 includes dispatcher command center 102 and/or event update computing device 114 (both shown in FIG. 1). In the example embodiment, user system 202 includes a processor 205 for executing instructions. In some embodiments, executable instructions are stored in a memory area 210. Processor 205 may include one or more processing units, for example, a multi-core configuration. Memory area 210 is any device allowing information such as executable instructions and/or written works to be stored and retrieved. Memory area 210 may include one or more computer-readable media.

User system 202 also includes at least one media output component 215 for presenting information to user 201. Media output component 215 is any component capable of conveying information to user 201. In some embodiments, media output component 215 includes an output adapter such as a video adapter and/or an audio adapter. An output adapter is operatively coupled to processor 205 and operatively couplable to an output device such as a display device, a liquid crystal display (LCD), organic light emitting diode (OLED) display, or "electronic ink" display, or an audio output device, a speaker or headphones. Stored in memory area 210 are, for example, computer readable instructions for providing a user interface (e.g., user interface 104, shown in FIG. 1) to user 201 via media output component 215 and, optionally, receiving and processing input from input device 220.

In some embodiments, user system 202 includes an input device 220 for receiving input from user 201. Input device 220 may include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output device of media output component 215 and input device 220. User system 202 may also include a communication interface 225, which is communicatively couplable to a remote device. Communication interface 225 may include, for example, a wired or wireless network adapter or a wireless data transceiver for use with a mobile phone network, Global System for Mobile communications (GSM), 3G, or other mobile data network or Worldwide Interoperability for Microwave Access (WIMAX).

Figure 3:
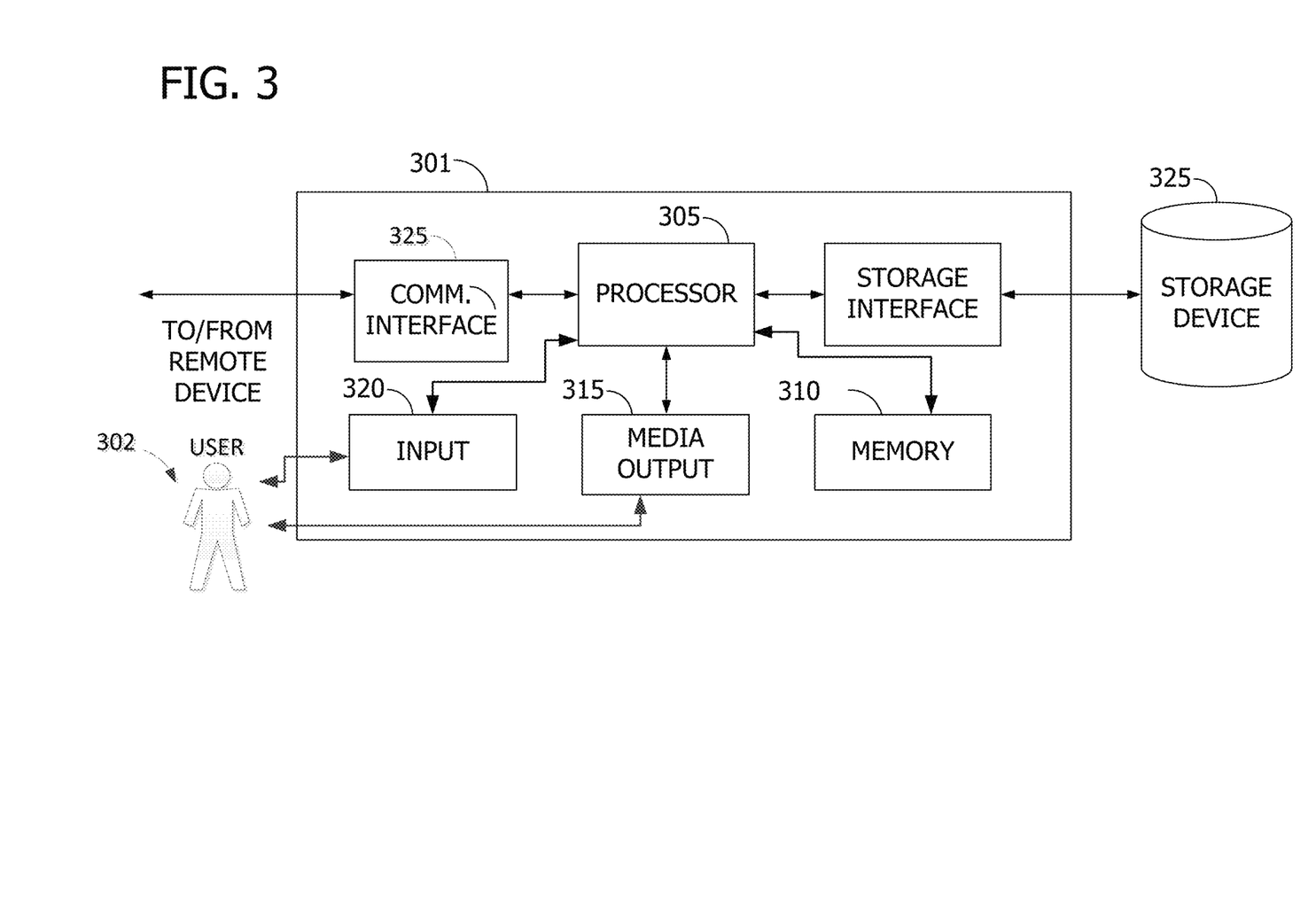
FIG. 3 illustrates an example configuration of a server computing device such as a dispatch command center as shown in FIG. 1.

FIG. 3 illustrates an example configuration of a server computing device 301 that may be accessed and/or operated by a user 302, such as dispatcher 110 (shown in FIG. 1). In some embodiments, computing device 301 may include dispatcher command center 102, payment processor 108, and/or event update computing device 114 (all shown in FIG. 1). In the example embodiment, computing device 301 includes a processor 305 for executing instructions. Processor 305 may include one or more processing units (e.g., in a multi-core configuration) for executing instructions. The instructions may be executed within a variety of different operating systems on the computing device 301, such as UNIX, LINUX, Microsoft Windows®, etc. It should also be appreciated that upon initiation of a computer-based method, various instructions may be executed during initialization. Some operations may be required in order to perform one or more processes described herein, while other operations may be more general and/or specific to a particular programming language (e.g., C, C #, C++, Java, or other suitable programming languages, etc.).

In some embodiments, executable instructions are stored in a memory area 310. Memory area 310 is any device allowing information such as executable instructions and/or written works to be stored and retrieved. Memory area 310 may include, but are not limited to, random access memory (RAM) such as dynamic RAM (DRAM) or static RAM (SRAM), read-only memory (ROM), erasable programmable read-only memory (EPROM), electrically erasable programmable read-only memory (EEPROM), and non-volatile RAM (NVRAM). The above memory types are exemplary only, and are thus not limiting as to the types of memory usable for storage of a computer program.

Computing device 301 also includes at least one media output component 315 for presenting information to user 302. Media output component 315 is any component capable of conveying information to user 302, and may be similar to media output component 215 (shown in FIG. 2). In some embodiments, media output component 315 includes an output adapter such as a video adapter and/or an audio adapter. An output adapter is operatively coupled to processor 305 and operatively couplable to an output device such as a display device, a liquid crystal display (LCD), organic light emitting diode (OLED) display, or "electronic ink" display, or an audio output device, a speaker or headphones.

In some embodiments, computing device 301 includes an input device 320 for receiving input from user 302. Input device 320 may be similar to input device 220 (shown in FIG. 2) and may include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output device of media output component 315 and input device 320. In other words, media output component 315 and input device 320 may collectively form user interface 104 (shown in FIG. 1). Computing device 301 may also include a communication interface 325, which is communicatively couplable to a remote device (e.g., another dispatcher command center 102 or payment processor 108). Communication interface 325 may include, for example, a wired or wireless network adapter or a wireless data transceiver for use with a mobile phone network, Global System for Mobile communications (GSM), 3G, or other mobile data network or Worldwide Interoperability for Microwave Access (WIMAX).

Stored in memory area 310 are, for example, computer readable instructions for providing a graphical user interface to user 302 via media output component 315 and, optionally, receiving and processing input from input device 320. A graphical user interface may include, among other possibilities, a web browser and client application. Web browsers enable users, such as user 302, to display and interact with media and other information typically embedded on a web page or a website. A client application allows user 302 to interact with a server application.

Processor 305 is operatively coupled to a communication interface 315 such that server system 301 is capable of communicating with a remote device such as user system 202 (shown in FIG. 2) or another server system 301. For example, communication interface 315 may receive requests from a user computing device 104 via the Internet, as illustrated in FIG. 1.

Processor 305 may also be operatively coupled to a storage device 325. Storage device 325 is any computer-operated hardware suitable for storing and/or retrieving data. In some embodiments, storage device 325 is integrated in server system 301. For example, server system 301 may include one or more hard disk drives as storage device 325. In other embodiments, storage device 325 is external to server system 301 and may be accessed by a plurality of server systems 301. For example, storage device 325 may include multiple storage units such as hard disks or solid state disks in a redundant array of inexpensive disks (RAID) configuration. Storage device 325 may include a storage area network (SAN) and/or a network attached storage (NAS) system.

In some embodiments, processor 305 is operatively coupled to storage device 134 via a storage interface 320. Storage interface 320 is any component capable of providing processor 305 with access to storage device 325. Storage interface 320 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 305 with access to storage device 325.

Figure 4:
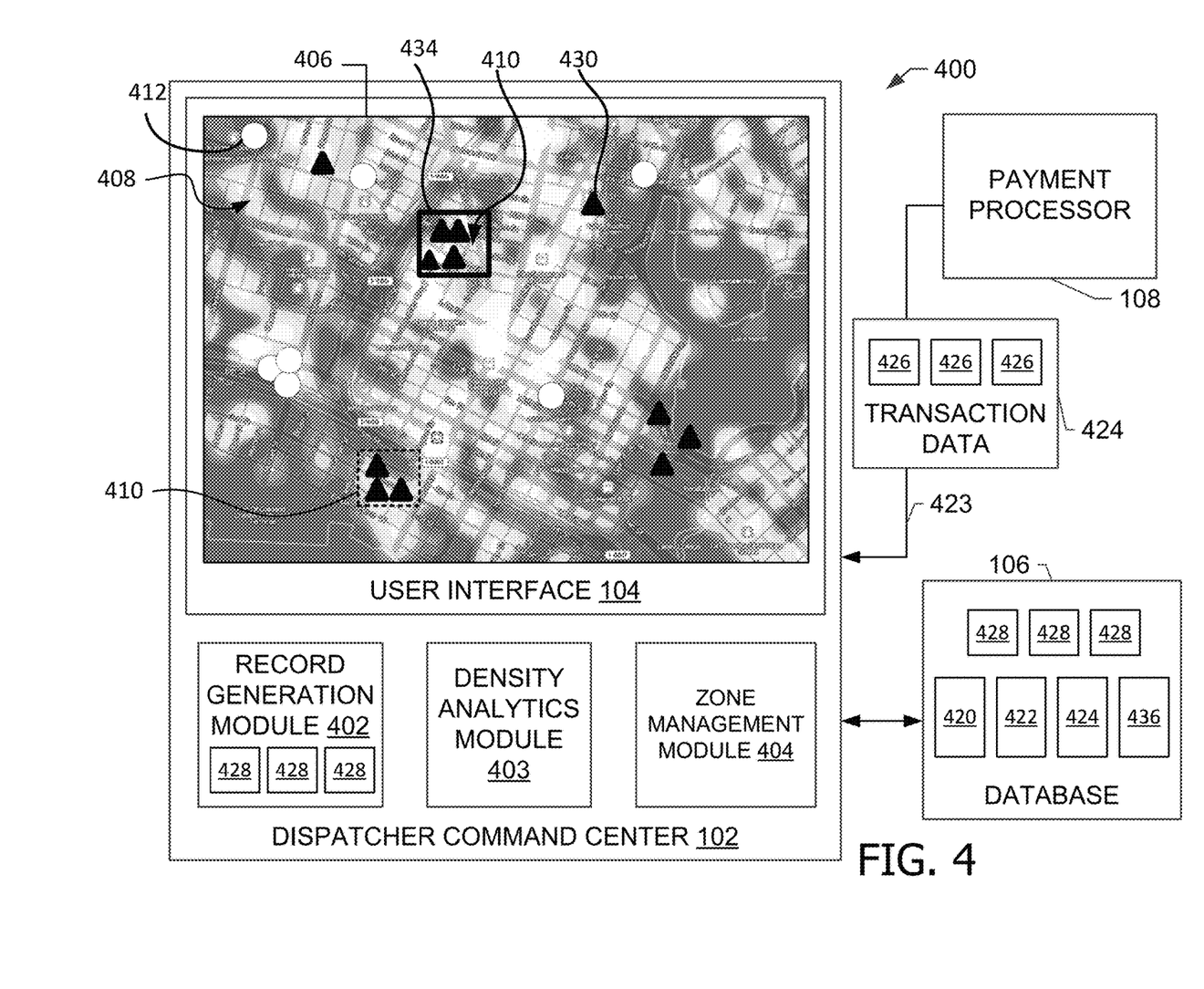
FIG. 4 is a data flow diagram illustrating the flow of data between various components of the ambulance deployment system shown in FIG. 1.

FIG. 4 is a data flow diagram 400 illustrating the flow of data between various components of ambulance deployment system 100 (shown in FIG. 1). In the illustrated embodiment, dispatcher command center 102 (shown in FIG. 1) includes user interface (UI) 104 (also shown in FIG. 1), a record generation module 402, a density analytics module 403, and a zone management module 404. Record generation module 402, density analytics module 403, and zone management module 404 may include computer-executable instructions implemented on a processor (e.g., processor 305, shown in FIG. 3) of dispatcher command center 102 to specifically execute the functions described herein.

UI 104 is configured to display a street map 406 of a coverage area 408. Coverage area 408 represents a geographical region or area covered by a particular emergency medical services (EMS) entity (e.g., a particular station, service, company, etc. responsible for providing EMS to coverage area 408). Zone management module 404 is configured to divide coverage area 408 into a plurality of zones 410. In one embodiment, zone management module 404 divides coverage area 408 into a plurality of zones 410 with equal area, for example, as a grid. In another embodiment, zone management module 404 divides coverage area 408 into zones 410 more contextually, for example, according to population density, number of buildings located therein, a number of blocks encompassed thereby, etc. In the illustrated embodiment, the boundaries of each zone 410 are not displayed on street map 406. However, in an alternative embodiment, the boundaries of each zone 410 are displayed on street map 406.

Density analytics module 403 is configured to process various information, as described herein, to control display of street map 406 and the population density representation thereon. In the illustrated embodiment, street map 406 is displayed as a heat map, wherein areas of "high heat" indicate locations or zones 410 with high population density (relative to other locations or zones 410 within coverage area 408). "High heat" may be represented with darker colors or shades, in certain embodiments, or with lighter colors or shades, in other embodiments. It should be understood that population density may be illustrated on street map 406 using representations other than a heat map. In the example embodiment, street map 406 further includes indicators 412 of locations of ambulances 112 (shown in FIG. 1) within coverage area 408. (It should be understood that various elements of street map 406 may not be illustrated to scale in order to provide clarity and simplicity to the depiction of street map 406 in FIG. 4.)

Dispatcher command center 102 is in communication with database 106 (shown in FIG. 1) such that dispatcher command center 102 may store information on and retrieve information from database 106. In the illustrated embodiment, database 106 stores historical population density information 420, emergency call records 422, and/or event records 436 thereon. Emergency call records 422 include historical and real-time emergency call records, including times and locations thereof. For example, historical and "current" or real-time dispatch or call records may be stored as a table, with times and locations of each call stored in cells associated with the corresponding call. Historical population density information 420 includes semi-empirical data related to the movement of people over the course of a day (e.g., that there is likely higher traffic in urban areas during employment hours, higher traffic in suburban areas during non-employment hours, known high-density events such as sporting events or concerts) and other probabilistic analyses that attempt to predict population density within coverage area 408 at various times of day and/or on various days of the week/month/year. Event records 436 include information about upcoming events parsed from available sources (e.g., newspapers, social media, newsletters, etc.). Event records 436 may include locations and times associated with events likely to draw relatively high numbers of people thereto, including, but not limited to, sporting events, concerts, conventions, plays, and other such events. As described herein with respect to FIG. 1, event records 436 may be received by dispatcher command center 102 from an event update computing device 114. Density analytics module 403 is configured to retrieve and process historical population density information 420, emergency call records 422, and event records 436, and display a representation of expected or likely population density within coverage area 408 on street map 406 (e.g., as a heat map, in the example embodiment).

In the example embodiment, payment processor 108 (shown in FIG. 1) transmits a data signal 423 to dispatcher command center 102. Data signal 423 includes transaction data 424 associated with a plurality of financial transactions 426. Each transaction 426 includes an associated transaction time, merchant identifier, and location identifier. The location identifier may identify a location at which the corresponding transaction 426 was initiated, a location of the corresponding cardholder at the time transaction 426 was initiated, and/or a merchant location. In the example embodiment, each transaction 426 is initiated within coverage area 408. In other embodiments, one or more transaction 426 may have been initiated at a location not within coverage area 408. Dispatcher command center 102 may be configured to discard transaction data 424 including transactions 426 that were not initiated within coverage area 408. In some embodiments, dispatcher command center 102 substantially continuously receives transaction data 424 from payment processor 108. In other embodiments, for example, where dispatcher command center 102 (and/or network 105) has limited bandwidth, dispatcher command center 102 may receive transaction data 424 at intervals (e.g., every minute, every 15 minutes).

Dispatcher command center 102 is configured to store transaction data 424 in database 106. In addition, dispatcher command center 102 is configured to process transaction data 424, in the example embodiment, using record generation module 402. Record generation module 402 is configured to parse the received transaction data 424 and generate a transaction record 428 associated with each transaction 426. Each transaction record 428 includes the associated time and transaction location of the transaction 426. Each transaction record 428 may further include an expiration time. The expiration time identifies a time that the corresponding transaction record 428 should be discarded and/or cleared from display on street map 406, as described further herein. Record generation module 402 may calculate an expiration time for a transaction record 428 by adding a predetermined constant time interval to the transaction time (e.g., 15 minutes, 30 minutes, 4 hours, etc.). Additionally or alternatively, record generation module 402 may calculate the expiration time for a transaction record 428 by adding a non-constant time interval to the transaction time. For example, the added time interval may be shortened or lengthened according to a number of transaction records 428 generated within a period of time (e.g., according to a frequency of transactions 426) and/or a number of transaction records 428 generated that are associated with a particular zone 410 within coverage area 408 (e.g., according to a density of transactions 426).

Density analytics module 403 is configured to process generated transaction records 428 for display on street map 406. In some embodiments, density analytics module 403 displays the transaction records 428 as an enhancement or update to the representation of population density already displayed on street map 406. "Enhanced display device" and/or "enhanced street map," as used herein, refers generally to this combination display of real-time and historical population density. Although not shown in the example embodiment, UI 104 may be configured to display a secondary street map alongside or otherwise adjacent to (primary) street map 406. Accordingly, wherein the following description refers to information displayed on "street map 406," such reference may include display on either or both a primary street map 406 and a secondary street map (not shown). In the illustrated embodiment, density analytics module 403 is configured to display transaction records 428 on street map 406 as a representation of real-time population density within coverage area 408. Density analytics module 403 may display an updated or "enhanced" street map 406 which includes a hybrid or combination of the representation of historical population density enhanced by the representation of real-time population density. In one embodiment, as shown, density analytics module 403 may facilitate display of individual transaction records 428 using discrete record indicators 430 on street map 406. However, in some cases, displaying individual record indicators 430 for each transaction record 428 processed by density analytics module 403 may overcrowd street map 406. Accordingly, in some embodiments, each record indicator 430 may represent a plurality of transaction records 428 (e.g., 10, 50, or 100 transactions).

In another embodiment, rather than displaying record indicators 430, density analytics module 403 may be configured to process transaction records 428 and determine how a frequency and/or density of transaction records 428 may augment the "heat" of the displayed heat map. Density analytics module 403 may then adjust the heat of the displayed heat map to correspond to the likely population density as indicated by the density and/or frequency of generated transaction records 428. In some embodiments, density analytics module 403 may implement both a "heat-adjustment" and a record-indicator method of displaying transaction records 428 to dispatcher 110 (shown in FIG. 1) using UI 104. In any embodiment, density analytics module 403 is configured to represent real-time population density within coverage area 408 using transaction record 428, such that dispatcher 110 may use the displayed street map 406 to readily identify areas of current high population density and deploy ambulances 112 accordingly. Density analytics module 403 is further configured to remove record indicators 430 and/or decrease "heat" according to the expiration times of transaction records 428 represented on street map 406. In some embodiments, density analytics module 403 may further instruct database 106 to delete any copy of any expired transaction record(s) 428 after the expiration time associated therewith, in order to save memory of database 106.

In certain embodiments, zone management module 404 is configured to generate alerts 434 for particularly high-density zones 410, as high-density zones 410 may require additional and/or more prompt response from ambulances 112. Zone management module 404 is configured to map generated transaction records 428 to zones 410 within coverage area 408. In one embodiment, zone management module 404 increments a counter associated with each zone 410, for each transaction record 428 having a transaction location within that zone 410. Zone management module 404 is further configured to define a high-density condition. If a zone 410 meets the high-density condition, the zone 410 is identified as a "high-density zone" 410. The high-density condition may include a threshold value reached by the counter for the zone 410. Upon the identification of a high-density zone 410, zone management module 404 generates an alert 434 for display on UI 104. In one embodiment, as illustrated, the alert 434 may be displayed on street map 406. Alert 434 may identify the high-density zone 410 by highlighting the boundary thereof. Additionally or alternatively, alert 434 may include a textual description or identification of the high-density zone 410 (e.g., "High traffic at 5$^{th}$ and Elm"). Alert 434 may be displayed on street map 406 with respect to the historical representation of the population density on street map 406, with respect to the real-time representation of the population density on street map 406, and/or with respect to an enhanced street map 406 including both the historical and real-time representations.

Figure 5:
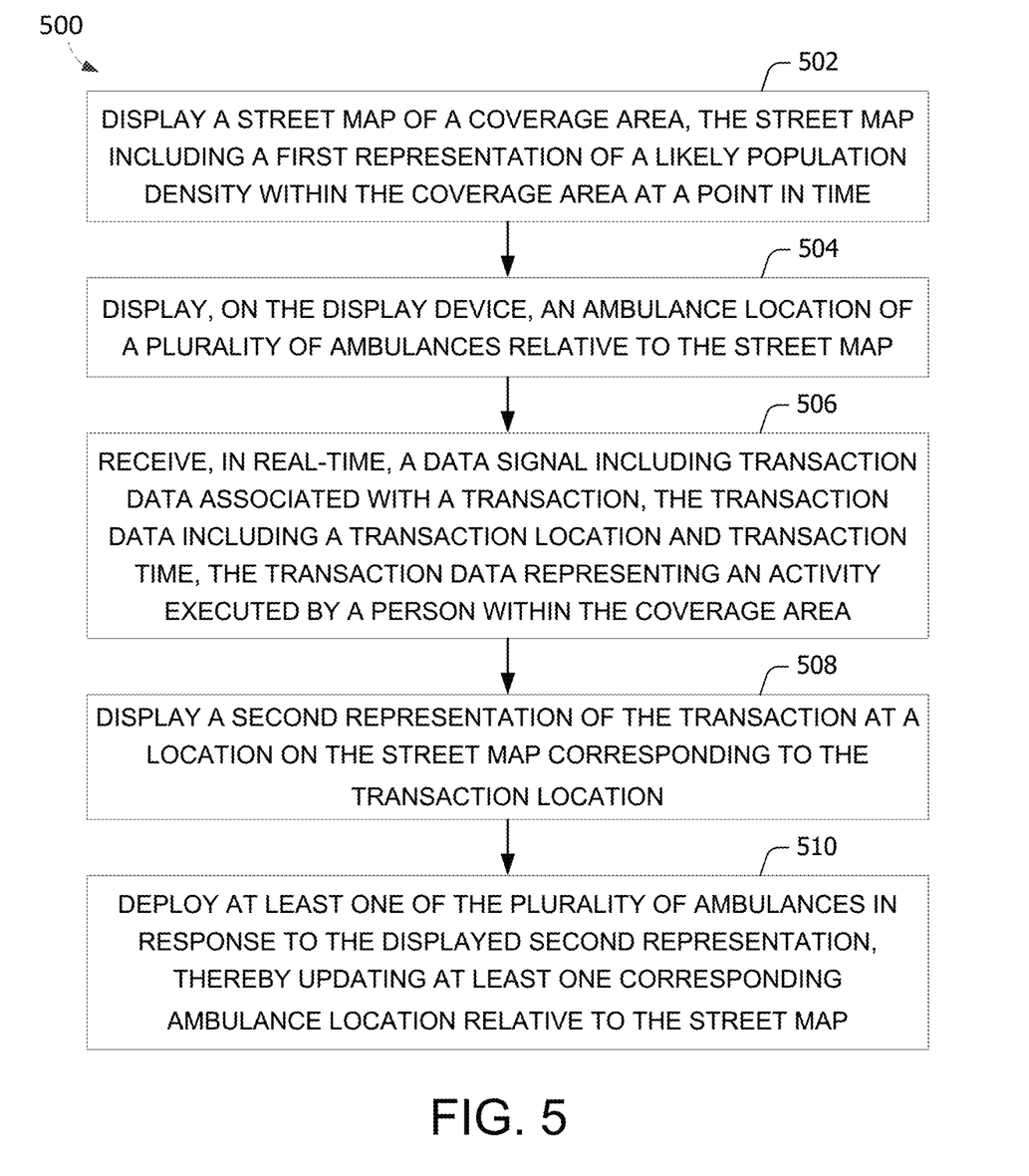
FIG. 5 is a flowchart of an example method for dynamically deploying ambulances using the ambulance deployment system shown in FIG. 1.

FIG. 5 is an example method 500 for dynamically deploying ambulances based on population density. In the example embodiment, method 500 is performed by a computing system such as dispatcher command center 102 (shown in FIGS. 1 and 4). Method 500 includes displaying 502 a street map (e.g., street map 406) of a coverage area (e.g., coverage are 408, both shown in FIG. 4). The street map includes a first representation of a likely population density within the coverage area at a point in time. In the example embodiment, the street map is displayed 502 on a display device of a computing device (e.g., dispatcher command center 102). Method 500 also includes displaying 504 an ambulance location (e.g., ambulance location 412, also shown in FIG. 4) of a plurality of ambulances relative to the street map. In the example embodiment, the ambulance locations of the plurality of ambulances are displayed 504 on the display device.

Method 500 further includes receiving 506, in real-time, a data signal (e.g., signal 423) including transaction data (e.g., transaction data 424) associated with a transaction (e.g., a transaction 426, all shown in FIG. 4). In the example embodiment, the transaction data includes a transaction location and transaction time. Moreover, the transaction data represents an activity executed by a person within the coverage area. Method 500 also includes displaying 508 a second representation of the transaction at a location on the street map corresponding to the transaction location (e.g., record indicator 430, shown in FIG. 4). In the example embodiment, the second representation of the transaction is displayed 508 on the display device. Method 500 further includes deploying 510 at least one of the plurality of ambulances in response to the displayed second representation, thereby updating at least one corresponding ambulance location relative to the street map. In some embodiments, the deploying 510 may be performed "automatically." For example, dispatcher command center 102, may transmit a deployment signal to the at least one ambulance, the deployment signal including instructions for a driver of the ambulance to move the ambulance. In some embodiments, the deploying 510 is performed "manually" by a user (e.g., dispatcher 110, shown in FIG. 1), for example, by contacting the driver of the ambulance via a radio, phone, or other communication channel and directing the driver to move the ambulance.

Figure 6:
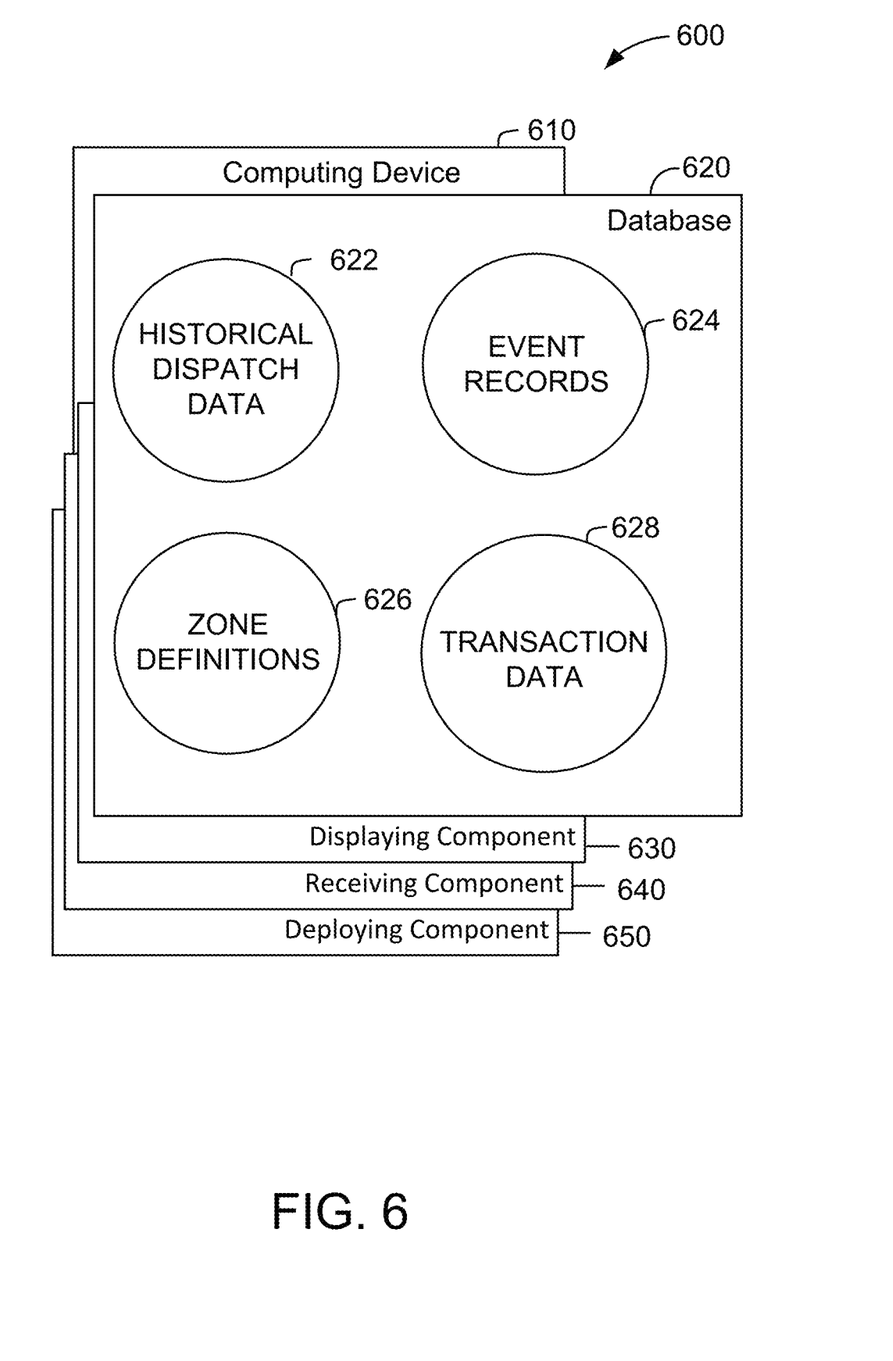
FIG. 6 shows a diagram of components of an example computing device that may be used in the ambulance system shown in FIG. 1 to facilitate dynamic ambulance deployment.

FIG. 6 shows a diagram of components 600 of an example computing device 610 that may be used in ambulance deployment system 100 shown in FIG. 1 to facilitate dynamic ambulance deployment based on population density. In some embodiments, computing device 610 is similar to dispatcher command center 102 (shown in FIGS. 1 and 4). Database 620 is coupled to several separate components within computing device 610, which perform specific tasks. Database 620 may be similar to database 106 (shown in FIG. 1) and is configured to store information. In the illustrated embodiment, database 620 stores (by way of example and not limitation) historical dispatch data 622 (which may include past emergency calls and/or semi-empirical data suggesting likely population density), event records 624, zone definitions 626, and transaction data 628.

Computing device 610 includes a displaying component 630. Displaying component 630 may be similar to any display device described herein, and is configured to display a street map of a coverage area, the street map including a first representation of a likely population density within the coverage area at a point in time. Displaying component 630 is also configured to display an ambulance location of a plurality of ambulances relative to the street map. Displaying component 630 is further configured to display a second representation of the transaction at a location on the street map corresponding to a transaction location of a plurality of transactions, as described herein.

Computing device 610 also includes a receiving component 640 configured to receive, in real-time, a data signal including transaction data (e.g., transaction data 628) associated with a transaction. In the example embodiment, transaction data 628 includes a transaction location and transaction time, and represents an activity executed by a person within the coverage area. It should be understood that receiving component 640 may receive other data signals including other data, as described herein, such as event data. Computing device 610 further includes a deploying component 650. Deploying component 650 is configured to deploy at least one of the plurality of ambulances in response to the displayed second representation, thereby updating at least one corresponding ambulance location relative to the street map. Deploying component 650 may include communication hardware and functionality such that deploying component 650 may automatically communicate with the at least one to-be-deployed ambulance (and/or a driver thereof) with deployment instructions. Deploying component 650 may additionally or alternatively be configured to communicate with dispatcher 110 (shown in FIG. 1) to convey deployment instructions thereto, such that dispatcher 110 may contact the to-be-deployed ambulance (and/or a driver thereof) with the deployment instructions.

As will be appreciated based on the foregoing specification, the above-described embodiments of the disclosure may be implemented using computer programming or engineering techniques including computer software, firmware, hardware or any combination or subset thereof, wherein the technical effect is a flexible system for various aspects of fraud analysis of payment card transactions. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium such as the Internet or other communication network or link. The article of manufacture containing the computer code may be made and/or used by executing the code directly from one medium, by copying the code from one medium to another medium, or by transmitting the code over a network.

In addition, although various elements of the dispatcher command center are described herein as including general processing and memory devices, it should be understood that the dispatcher command center is a specialized computer configured to perform the steps described herein for facilitating dynamic deployment of ambulances.

These computer programs (also known as programs, software, software applications, "apps", or code) include machine instructions for a programmable processor, and can be implemented in a high-level procedural and/or object-oriented programming language, and/or in assembly/machine language. As used herein, the terms "machine-readable medium" "computer-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The "machine-readable medium" and "computer-readable medium," however, do not include transitory signals. The term "machine-readable signal" refers to any signal used to provide machine instructions and/or data to a programmable processor.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A dispatcher command center for dynamic ambulance deployment based on population density, said dispatcher command center including a display device and a processor in communication with a memory, said processor programmed to:
   display, on the display device, a street map of a coverage area, the street map including a first representation of a likely population density within the coverage area at a point in time;
   display, on the display device, an ambulance location of a plurality of ambulances relative to the street map;
   receive, in real-time over an interval of time, a plurality of messages including payment card transaction data associated with a plurality of payment card transactions, the payment card transaction data including transaction location and transaction time information, the payment card transaction data representing locations of people within the coverage area during the interval of time;
   display, on the display device, a second representation illustrating real-time population density at locations on the street map corresponding to the transaction locations, wherein the real-time population density is updated in real-time over the interval of time based on the payment card transaction data; and
   deploy at least one of the plurality of ambulances in response to the displayed second representation of real-time population density, thereby updating at least one corresponding ambulance location relative to the street map.

2. The dispatcher command center of claim 1, wherein the plurality of messages are received from a payment processor, wherein each payment card transaction of the plurality of payment card transactions is performed by a cardholder and processed by the payment processor.

3. The dispatcher command center of claim 2, wherein said processor is further programmed to display, on the display device, respective representations of each payment card transaction of the plurality of payment card transactions on the street map.

4. The dispatcher commend center of claim 1, wherein the street map includes a heat map, and wherein the second representation includes an increased amount of heat at locations on the street map corresponding to transaction locations, wherein to deploy the at least one of the plurality of ambulances, said processor is further programmed to transmit a deployment signal to a respective operator of the at least one of the plurality of ambulances, the deployment signal including instructions to update the location of the at least one of the plurality of ambulances based on the real-time population density.

5. The dispatcher commend center of claim 1, wherein the street map is a primary street map and wherein said processor is further programmed to display the second representation on a secondary street map adjacent to the primary street map on the display device.

6. The dispatcher command center of claim 1, wherein said processor is further programmed to:
   display an enhanced street map including the first representation of likely population density enhanced by the second representation;
   divide the coverage area into a plurality of zones;
   for each payment card transaction of the plurality of payment card transactions, map the respective transaction location to a respective zone of the plurality of zones;
   define a high-density condition indicating high density within one zone relative to the others of the plurality of zones;
   for each zone meeting the high-density condition based on a number of transactions mapped thereto, generate an alert identifying the corresponding zone as a high-density zone;
   display the enhanced street map including the alert on the display device; and
   deploy at least one of the plurality of ambulances to the high-density zone.

7. A computer-implemented method for dynamically deploying ambulances based on population density using a dispatcher command center, the dispatcher command center including a display device and a processor in communication with a memory, said method comprising:
   displaying, on the display device, a street map of a coverage area, the street map including a first representation of a likely population density within the coverage area at a point in time;
   displaying, on the display device, an ambulance location of a plurality of ambulances relative to the street map;
   receiving, in real-time over an interval of time, a plurality of messages including payment card transaction data associated with a plurality of payment card transactions, the payment card transaction data including transaction location and transaction time information, the payment card transaction data representing locations of people within the coverage area during the interval of time;

displaying, on the display device, a second representation illustrating real-time population density at locations on the street map corresponding to the transaction locations, wherein the real-time population density is updated in real-time over the interval of time based on the payment card transaction data; and deploying at least one of the plurality of ambulances in response to the displayed second representation of real-time population density, thereby updating at least one corresponding ambulance location relative to the street map.

8. The computer-implemented method of claim 7, wherein the plurality of messages are received from a payment processor, wherein each payment card transaction of the plurality of payment card transactions is performed by a cardholder and processed by the payment processor.

9. The computer-implemented method of claim 8 further comprising displaying, on the display device, respective representations of each payment card transaction of the plurality of payment card transactions on the street map.

10. The computer-implemented method of claim 7, wherein the street map includes a heat map, and wherein displaying the second representation comprises increasing an amount of heat at locations on the street map corresponding to transaction locations, wherein deploying the at least one of the plurality of ambulances comprises transmitting a deployment signal to a respective operator of the at least one of the plurality of ambulances, the deployment signal including instructions to update the location of the at least one of the plurality of ambulances based on the real-time population density.

11. The computer-implemented method of claim 7, wherein the street map is a primary street map, said method further comprising displaying the second representation on a secondary street map adjacent to the primary street map on the display device.

12. The computer-implemented method of claim 7 further comprising:

displaying an enhanced street map including the first representation of likely population density enhanced by the second representation;

dividing the coverage area into a plurality of zones;

for each payment card transaction of the plurality of payment card transactions, mapping the respective transaction location to a respective zone of the plurality of zones;

defining a high-density condition indicating high density within one zone relative to the others of the plurality of zones;

for each zone meeting the high-density condition based on a number of transactions mapped thereto, generating an alert identifying the corresponding zone as a high-density zone;

displaying the enhanced street map including the alert on the display device; and deploying at least one of the plurality of ambulances to the high-density zone.

13. At least one non-transitory computer-readable storage media having computer-executable instructions embodied thereon, wherein when executed by at least one processor in communication with a memory, the computer-executable instructions cause the processor to:

display, on a display device, a street map of a coverage area, the street map including a first representation of a likely population density within the coverage area at a point in time;

display, on the display device, an ambulance location of a plurality of ambulances relative to the street map;

receive, in real-time over an interval of time, a plurality of messages including payment card transaction data associated with a plurality of payment card transactions, the payment card transaction data including transaction location and transaction time information, the payment card transaction data representing locations of people within the coverage area during the interval of time;

display, on the display device, a second representation illustrating real-time population density at locations on the street map corresponding to the transaction locations, wherein the real-time population density is updated in real-time over the interval of time based on the payment card transaction data; and deploy at least one of the plurality of ambulances in response to the displayed second representation of real-time population density, thereby updating at least one corresponding ambulance location relative to the street map.

14. The computer-readable storage media of claim 13, wherein the plurality of messages are received from a payment processor, wherein each payment card transaction of the plurality of payment card transactions is performed by a cardholder and processed by the payment processor.

15. The computer-readable storage media of claim 13, wherein the street map includes a heat map, and wherein the second representation includes an increased amount of heat at locations on the street map corresponding to transaction locations, wherein to deploy the at least one of the plurality of ambulances, the computer-executable instructions further cause the processor to transmit a deployment signal to a respective operator of the at least one of the plurality of ambulances, the deployment signal including instructions to update the location of the at least one of the plurality of ambulances based on the real-time population density.

16. The computer-readable storage media of claim 13, wherein the street map is a primary street map and wherein the computer-executable instructions further cause the processor to display the second representation on a secondary street map adjacent to the primary street map on the display device.

17. The computer-readable storage media of claim 13, wherein the computer-executable instructions further cause the processor to:

display an enhanced street map including the first representation of likely population density enhanced by the second representation;

divide the coverage area into a plurality of zones;

for each payment card transaction of the plurality of payment card transactions, map the respective transaction location to a respective zone of the plurality of zones;

define a high-density condition indicating high density within one zone relative to the others of the plurality of zones;

for each zone meeting the high-density condition based on a number of transactions mapped thereto, generate an alert identifying the corresponding zone as a high-density zone;

display the enhanced street map including the alert on the display device; and deploy at least one of the plurality of ambulances to the high-density zone.

\* \* \* \* \*